United States Patent [19]

Osaka et al.

[11] Patent Number: 4,929,330
[45] Date of Patent: May 29, 1990

[54] DIFFUSION-LIMITING MEMBRANE HOLDING MEANS FOR SENSOR

[75] Inventors: Tatsuhiko Osaka, Kurita; Hiroshi Terawaki, Kouka; Mitsunari Okamoto, Sakai, all of Japan

[73] Assignee: Daikin Industries, Ltd., Osaka, Japan

[21] Appl. No.: 423,533

[22] Filed: Oct. 16, 1989

Related U.S. Application Data

[63] Continuation of Ser. No. 176,287, Mar. 31, 1988, abandoned.

[30] Foreign Application Priority Data

Mar. 31, 1987 [JP] Japan .................. 62-49736
Apr. 30, 1987 [JP] Japan .................. 62-65508
Apr. 30, 1987 [JP] Japan .................. 62-65507
Dec. 26, 1987 [JP] Japan .................. 62-197711
Dec. 26, 1987 [JP] Japan .................. 62-197708

[51] Int. Cl.$^5$ ............................ G01N 27/30
[52] U.S. Cl. ............................ 204/402; 204/403; 204/415; 435/291; 435/817
[58] Field of Search ............ 204/403, 1 E, 402, 415, 204/407; 435/817, 291

[56] References Cited

U.S. PATENT DOCUMENTS 4,175,028 11/1979 Payton .................. 204/296
4,757,022 7/1988 Shults et al. .......... 435/291

FOREIGN PATENT DOCUMENTS 0237879 3/1987 European Pat. Off. .
2095409 9/1982 United Kingdom .

OTHER PUBLICATIONS

Research Disclosure, 19040, (Feb. 1980).

Primary Examiner—G. L. Kaplan
Attorney, Agent, or Firm—Beveridge, DeGrandi & Weilacher

[57] ABSTRACT

A diffusion-limiting membrane holding means for a sensor comprising: a slender resilient thin plate, of which one shorter side serves as an engagement side, and of which one longer side is provided at its predetermined position with an engagement portion, an opening being formed in the thin plate between the engagement side and the engagement portion; and a diffusion-limiting membrane integrally attached to the thin plate as covering the opening; whereby the resliency of the thin plate causes the diffusion-limiting membrane to be stuck to the surface of an enzyme electrode unit of a sensor, thus enhancing the accuracy of concentration measurement of a target substance to be measured.

22 Claims, 9 Drawing Sheets

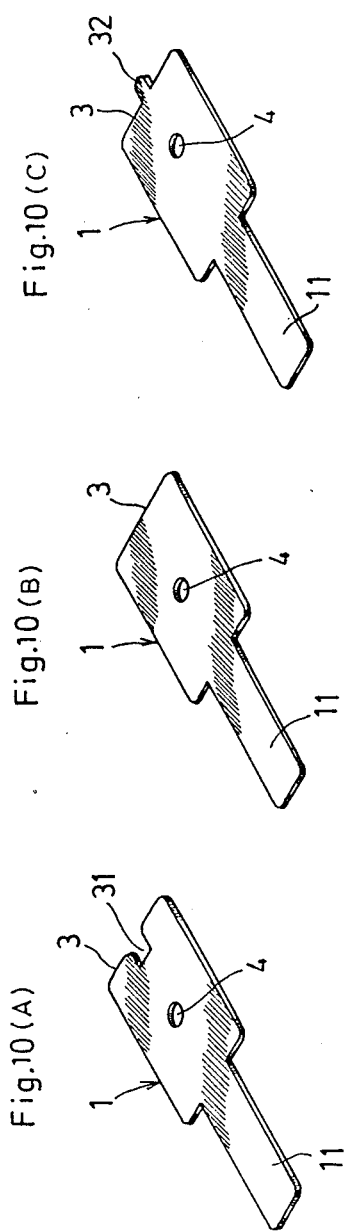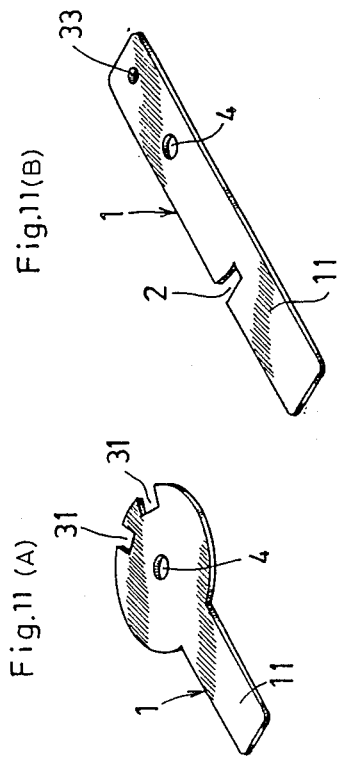

DIFFUSION-LIMITING MEMBRANE HOLDING MEANS FOR SENSOR

This application is a continuation, of application Ser. No. 07/176,287, filed Mar. 31, 1988 and now abandoned.

BACKGROUND OF THE INVENTION

The present invention relates to a diffusion-limiting membrane holding means for a sensor, and more particularly to a diffusion-limiting membrane holding means for a sensor suitably used for sticking a diffusion-limiting membrane to the surface of an enzyme electrode unit of a sensor.

It is known that a physiologic active substance has a characteristic capable of selectively detecting a very complicated organic compound, protein or the like with high sensitivity. With attention directed to this characteristic, researches and developments have been made on measurement of such organic compound, protein or the like with the use of an enzyme electrode unit having base electrodes on which a physiologic active substance is immobilized.

When measuring a target substance with the use of the enzyme electrode unit above-mentioned, the target substance is oxidized or reduced under the presence of such physiologic active substance. The concentration of the target substance is determined by measuring the amount of a substance produced or consumed in such oxidation or reduction. Accordingly, the upper limit of concentration which can be measured, is determined dependent on the amount of a substance provoking such oxidation or reduction, for example the amount of oxygen.

In view of the foregoing, it has been proposed to increase the concentration measuring limit by limiting the penetration rate of a target substance by a diffusion-limiting membrane mounted on the surface of an enzyme-immobilized membrane in/on which a physiologic active substance is immobilized.

More specifically, there has been adopted an arrangement in which the diffusion-limiting membrane is mounted on a cap to be threadedly secured to the base portion of a rod-like enzyme electrode unit, and screwing the cap causes the diffusion-limiting membrane to be automatically stuck to the enzyme-immobilized membrane.

With the use of such arrangement, the penetration rate of a target substance to be measured is limited by the diffusion-limiting membrane, thereby to achieve measurement of a considerably high concentration. To eliminate the influence of interfering substances contained in a target solution to be measured (for example, increase in diffusion limiting effect resulting from the sticking of such interfering substances), the diffusion-limiting membrane needs to be replaceable. This is the reason of why the membrane screwing mechanism by a cap is adopted.

When the diffusion-limiting membrane holding means having the arrangement above-mentioned is used, replacement of the diffusion-limiting membrane may be relatively facilitated. There are instances, however, where it becomes very difficult to mount or remove the holding means on or from the base portion of an enzyme electrode unit due to the arrangement of its mounting mechanism, or where it is not possible to achieve a uniform adhesion of the diffusion-limiting membrane to the enzyme-immobilized membrane due to the degree of the screwing force.

Further, when the enzyme electrode unit base portion has a small diameter, resulting in decrease in cap size, this causes the manual mounting/removal operation to be very difficult. This makes the problems above-mentioned more conspicuous.

Moreover, the diffusion-limiting membrane is mounted on a cap, requiring a large space for preserving and/or transportiong the same.

Further, the enzyme electrode unit has a convex curved surface having a predetermined radius of curvature, while the diffusion-limiting membrane mounting surface of the cap is made in a plane surface having neither convex nor concave portions. Accordingly, the diffusion-limiting membrane is forcibly press-contacted with the surface of the enzyme electrode unit by force exerted on only the edge of an opening through which a target solution to be measured penetrates. Therefore, the diffusion-limiting membrane or the enzyme-immobilized membrane secured to the surface of the enzyme electrode unit is susceptible to damages.

A pressing force of the diffusion-limiting membrane to the enzyme-immobilized membrane is exerted only in points or in a line. This assures no uniform contact therebetween throughout the surfaces. Accordingly, when the diffusion-limiting membrane is replaced, measured data may vary to deteriorate the reproducibility.

Further, a target solution to be measured is guided to the diffusion-limiting membrane through a relatively small opening formed in the diffusion-limiting membrane holding means. This requires to accurately set the dropping position of the target solution, decreasing the operational efficiency.

More specifically, the diffusion-limiting membrane holding means may be hydrophilic or hydrophobic dependent on the material thereof.

When the holding means is hydrophilic, not only that surface of the diffusion-limiting membrane holding means on which a target solution to be measured is dropped, but also the wall of the opening through which the target solution to be measured penetrates, are hydrophilic. If the amount of a target solution to be measured is small, a major portion of the target solution is not guided to the opening but diffuses on the top surface of the diffusion-limiting membrane holding means. This decreases the utility efficiency of the target solution to be measured.

On the contrary, when the holding means is hydrophobic, a target solution to be measured is apt to be repelled by the diffusion-limiting membrane holding means. Accordingly, there is considerably reduced the possibility that the target solution is smoothly guided to the diffusion-limiting membrane through a relatively small opening.

Prior to actual concentration measurement of a target substance, a necessary amount of a standard solution for calibration contained in a vessel is dropped on the diffusion-limiting membrane to obtain a detection signal, based on which an initial calibration operation is then made. In particular, to facilitate the dropping of the standard solution for calibration onto the diffusion-limiting membrane, it may be proposed that the standard solution for calibration contained in the vessel is dropped by pressing the vessel body.

Thus, there are required a target substance concentration measuring apparatus and a vessel for containing a standard solution for calibration, making the measurement very expensive in its entirety. Further, various germs may stick to the vessel to change the concentration of the standard solution for calibration. More specifically, the vessel for containing a standard solution for calibration generally contains a much greater amount of the standard solution or calibration than an amount required for one initial calibration operation. This makes the vessel considerably bulky. Further, with a standard solution for calibration contained therein, the vessel needs to be preserved for a relatively long period of time. If various germs stick to the vessel in such preservation period, substances in the standard solution may be consumed by such various germs. Accordingly, the target substance in the standard solution may be decreased in concentration with the passage of time. This makes it impossible to use such solution as a standard solution for calibration. To prevent the occurrence of such problems, it is required not only to suitably arrange the vessel preserving environment, but also to use care such that the vessel does not come in contact with the cap or the like when the standard solution is dropped. This remarkably decreases the operational efficiency.

SUMMARY OF THE INVENTION

It is an object of the present invention to provide a diffusion-limiting membrane holding means for a sensor which considerably simplfies the operation of mounting and removing a diffusion-limiting membrane.

It is another object of the present invention to provide a diffusion-limiting membrane holding means for a sensor which assures a uniform adhesion of a diffusion-limiting membrane to an enzyme-immobilized membrane.

It is a further object of the present invention to provide a diffusion-limiting membrane holding means for a sensor which simplifies the operation of lifting up a diffusion-limiting membrane.

It is still another object of the present invention to provide a diffusion-limiting membrane holding means for a sensor which assures a uniform contact of a diffusion-limiting membrane with the surface of an enzyme electrode unit.

It is a still further object of the present invention to provide a diffusion-limiting membrane holding means for a sensor which prevents an enzyme-immobilized membrane from being deteriorated in characteristics due to mounting and/or removal of a diffusion-limiting membrane.

It is yet still another object of the present invention to provide a diffusion-limiting membrane holding means for a sensor which smoothly guides a target solution to be measured which has been dropped, to a diffusion-limiting membrane.

It is a yet still further object of the present invention to provide a diffusion-limiting membrane holding means for a sensor which simplifies the operation of dropping a standard solution for calibration.

In order to achieve the objects above-mentioned, the diffusion-limiting membrane holding means for a sensor in accordance with the present invention comprises:

a thin resilient plate provided in a predetermined position thereof with an opening through which a target solution to be measured is adapted to penetrate; and a diffusion-limiting membrane for limiting diffusion of the target solution attached to the thin resilient plate as covering the opening.

Preferably, the diffusion-limiting membrane holding means for a sensor comprises;

a thin resilient plate lengthened in one direction, which is provided at its predetermined position with an opening through which a target solution to be measured is adapted to penetrate; and a diffusion-limiting membrane for limiting diffusion of the target solution attached to the thin resilient plate as covering the opening;

one longitudinal end side of the thin plate serving as an engagement side which is adapted to be engaged with one of a pair of positioning portions which are disposed on a sensor, the positioning portions being opposite to each other with respect to an enzyme electrode unit of the sensor;

the other longitudinal end side of the thin plate serving as a holding portion;

one longer side of the thin plate provided at its predetermined position with an engagement portion adapted to be engaged with the other of the pair of positioning portions.

Preferably, the thin plate is provided at its predetermined position with a projecting portion for holding one longitudinal end side of the thin plate as raised.

Preferably, the thin plate is provided at its predetermined area including the opening with a concave portion having the substantially the same radius of curvature as that of the surface of an enzyme electrode unit of a sensor.

Preferably, only the wall of the opening is hydrophilic.

Preferably, there is formed a housing portion for housing a standard solution for calibration which is adapted to supply the standard solution to the opening.

According to the diffusion-limiting membrane holding means for a sensor having the arrangement above-mentioned, the thin resilient plate may be contacted to the enzyme electrode unit so as to be positioned the opening with respect to the enzyme electrode unit. Then, the thin resilient plate may be resiliently bent to enable the diffusion-limiting membrane to be securely stuck to the surface of the enzyme electrode unit.

When the thin resilient plate is lengthened in one direction, with the holding portion held with the hand, one longitudinal end side of the thin resilient plate lengthened in one direction may be engaged with one of a pair of positioning portions disposed on a sensor. Then, the engagement portion formed at a predetermined position of one longer side may be engaged with the other of the positioning portions. Accordingly, the opening may be accurately positioned with respect to the enzyme electrode unit, and the thin resilient plate may be resiliently bent to enable the diffusion-limiting membrane to be securely stuck to the surface of the enzyme electrode unit.

In such state, a target solution to be measured is allowed to penetrate through the opening, causing a target substance in the solution to be limited in diffusion by the diffusion-limiting membrane. An electric signal corresponding to the concentration of the target substance thus limited in diffusion may be taken out from the enzyme electrode unit.

When the thin resilient plate is provided at its predetermined position with a projecting portion for holding one end side of the thin resilient plate as raised, the thin resilient plate as put at an arbitrary place may be easily lifted up. Further, even though a target substance to be measured is dropped with the diffusion-limiting membrane holding means at an arbitrary place, there may be considerably reduced the possibility that such place is wetted by the target solution.

When the thin resilient plate is provided at its predetermined area including the opening with a concave portion having the substantially same radius of curvature as that of the surface of the enzyme electrode unit, it is prevented that a pressing force is only locally applied to the surface of the enzyme electrode unit. This assures uniform application of a pressing force throughout the surface of the enzyme electrode unit. Consequently, this prevents the deterioration of the characteristics of an enzyme-immobilized membrane due to falling-off of an immobilized enzyme.

When only the wall of the opening is hydrophilic, a target solution to be measured may be securely guided to the opening. This may not only eliminate the need to enhance so much the accuracy of a position to which a target solution to be measured is dropped, but also decrease the amount of target solution to be dropped.

When the the diffusion-limiting membrane holding means for a sensor is provided with a housing portion for housing a standard solution for calibration which is adapted to supply the standard solution to the opening, it is not required to specially prepare vessel for containing a standard solution for calibration. This generally simplifies a calibration operation.

Other objects, advantages and novel characteristics of the present invention will be apparent from the following description.

BRIEF DESCRIPTION OF THE DRAWINGS

FIGS. 10a, b and c and FIG. 11a and b are perspective views of a diffusion-limiting membrane holding means for a sensor in accordance with fifth and sixth embodiments of the present invention, respectively;

DESCRIPTION OF THE PREFERRED EMBODIMENTS

Figure 1:
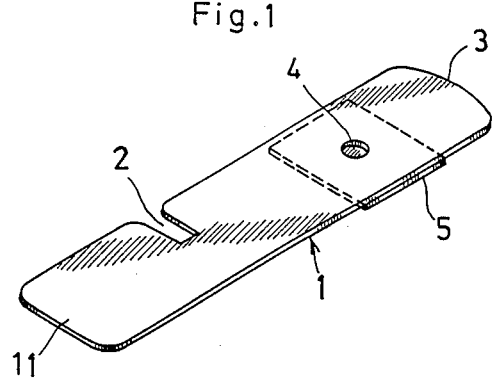
FIG. 1 is a perspective view of a diffusion-limiting membrane holding means for a sensor in accordance with a first embodiment of the present invention.
Figure 2:
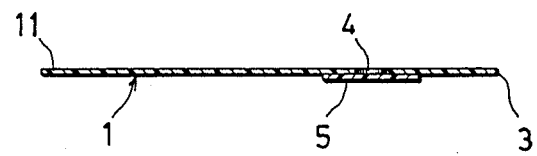
FIG. 2 is a vertical section view of the center portion of the means in FIG. 1.

FIG. 1 is a perspective view of a first embodiment of the diffusion-limiting membrane holding means for a sensor in accordance with the present invention, while FIG. 2 is a vertical section view thereof.

In FIGS. 1 and 2, the means has a relatively resilient thin resilient plate 1 substantially in the form of a rectangle which has resistance against a target solution to be measured. The thin plate 1 has a square engagement cutaway portion 2 at the center of one longer side thereof. One shorter side 3 is arcuate. The plate 1 has a circular opening 4 of which center is positioned at the center of a circle including the arc. A diffusion-limiting membrane 5 is attached to the underside of the thin resilient plate 1 with adhesives or by other suitable means, such that the opening 4 is covered by this membrane 5. That portion of the thin resilient plate 1 which is located in the vicinity of the other shorter side, serves as a holding portion 11.

Figure 3:
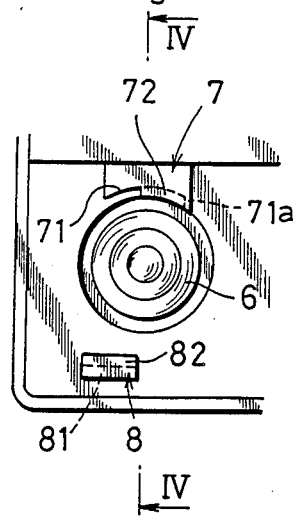
FIG. 3 is a plan view of main portions of a sensor on which the diffusion-limiting membrane for sensor of the present invention is mounted.
Figure 4:
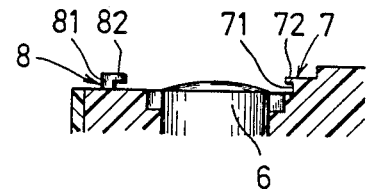
FIG. 4 is a longitudinal section view taken along the line IV—IV of FIG. 3.

FIG. 3 is a plan view of main portions of a sensor on which the diffusion-limiting membrane holding means of the present invention is to be mounted, while FIG. 4 is a longitudinal section view thereof.

The sensor has a base stand, an enzyme electrode unit 6 mounted at a predetermined position of the base stand such that the electrode unit surface projects upward, and engagement portions 7 and 8 opposite to each other with respect to the the enzyme electrode unit 6.

More specifically, the engagement portion 7 has an engagement concave 71 of which inner part has an arcuate surface having the same radius of curvature as that of the shorter side 3 of the thin resilient plate 1. The engagement portion 7 also has a projection 72 which constitutes an upper regulating projection of the engagement concave 71. The engagement concave 71 is provided at a predetermined position in the vicinity of the end thereof with a stopper 71a for regulating the rotation of the thin resilient plate 1. The projection 72 may have a wide width covering the entire width of the engagement concave 71, or may have a width narrower than the entire width of the engagement concave 71. The engagement portion 8 has a standing portion 81 having a width substantially equal to the width of the engagement cutaway portion 2, and an upper regulating projection 82 extending in one direction from the upper portion of the standing portion 81. The enzyme electrode unit 6 has a substantially arcuate surface.

A diffusion-limiting membrane attached to the diffusion-limiting membrane holding means of the present invention, may be mounted on the a sensor having the arrangement above-mentioned in the following manner.

Figure 5C:
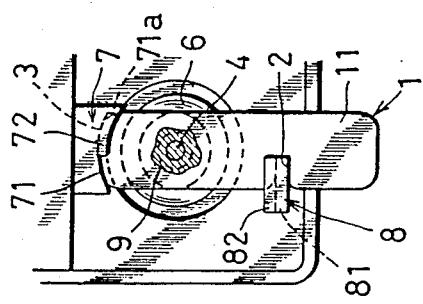
FIGS. 5a, b and c are views illustrating how to mount a diffusion-limiting membrane for sensor.
Figure 5B:
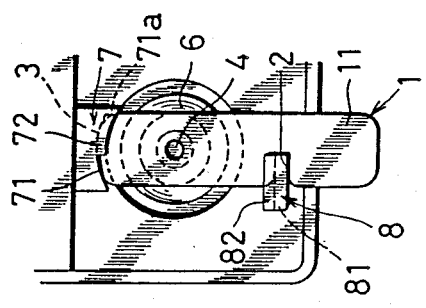
Figure 5A:
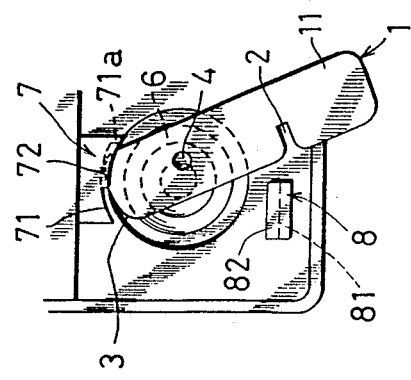

With the diffusion-limiting membrane 5 positioned at the underside of the thin resilient plate 1, the shorter side 3 of the thin resilient plate 1 is inserted into the engagement concave 71 (At this time, the center of the opening 4 is positionally shifted from the center of the enzyme electrode unit 6 as shown in FIG. 5 (A)). With the thin plate 1 resiliently bent such that the diffusion-limiting membrane 5 sticks to the surface of the enzyme electrode unit 6, the thin plate 1 is rotated in a direction such that the engagement cutaway portion 2 is engaged with the engagement portion 8. The upper regulating projection 82 of the engagement portion 8 prevents the thin resilient plate 1 from being restored to a non-bent state (See FIG. 5 (B)). This permits the diffusion-limiting membrane 5 to be stuck to the enzyme electrode unit 6 while being held at an accurate relative position with respect thereto.

Then, a target solution to be measured 9 is dropped on the thin resilient plate 1 at its predetermined area including the opening 4, as shown in FIG. 5 (C). The target solution 9 is guided to the diffusion-limiting membrane 5 through the opening 4. The solution then reaches to the enzyme electrode unit 6 with a target substance therein limited in diffusion by the diffusion-limiting membrane 5 to lower the concentration of the target substance to some degree. Accordingly, even though the concentration of a target substance to be measured in a target solution is originally high, a concentration measurement of the target solution can be made with the concentration of the target substance considerably lowered. Thus, the concentration measuring limit can be increased.

After the measurement has been finished, the thin resilient plate 1 may be easily removed by reversing the mounting operations mentioned earlier.

In the embodiment above-mentioned, it is preferable that the thin resilient plate 1 has a surface having hydrophobic property while only the wall of the opening 4 is hydrophilic. Such arrangement prevents the target solution to be measured 9 which has been dropped, from remaining on the surface of the thin resilient plate 1, enabling the solution 9 to be smoothly guided to the opening 4. More specifically, the thin resilient plate 1 may be made of, for example, polyester having hydrophilic property, and the surface of the thin resilient plate 1 may be treated with fluoroplastics or silicone, thereby to obtain a diffusion-limiting membrane holding means for a sensor in which only the wall of the opening 4 is hydrophilic.

As apparent from the foregoing, the replaceable diffusion-limiting membrane 5 is attached to the thin resilient plate 1, thus considerably reducing the entire thickness of the holding means. Accordingly, even though a number of holding means are stacked, the entire bulkiness can be lowered. This enables a number of the holding means to be preserved and/or transported in a small space.

Figure 6:
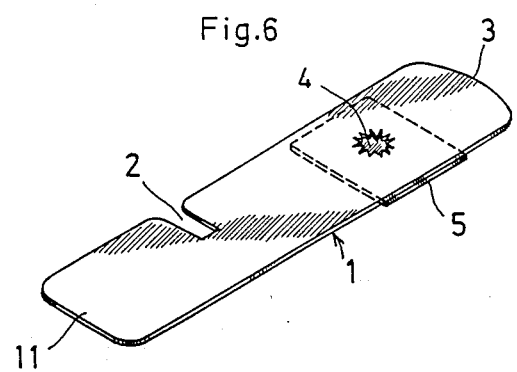
FIG. 6 to FIG. 8 are perspective views of a diffusion-limiting membrane holding means for a sensor in accordance with second, third and fourth embodiments of the present invention, respectively.

FIG. 6 is a perspective view of a second embodiment of the holding means of the present invention. The second embodiment is the same as the first embodiment in FIG. 1, except that the periphery of an opening 4 in the second embodiment has a number of convexo-concave portions.

In the second embodiment, even though the wall of the opening 4 has no high hydrophilic nature, a target solution to be measured 9 can be smoothly guided to the opening 4.

Figure 7:
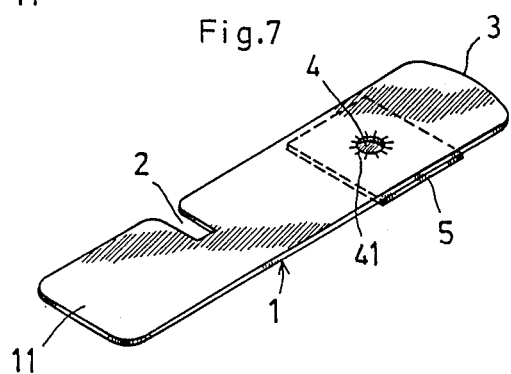

FIG. 7 is a perspective view of a third embodiment of the present invention. The third embodiment is the same as the second embodiment, except that the third embodiment has a plurality of grooves 41 formed at the periphery of an opening 4, the grooves 41 extending around the opening 4.

In the third embodiment also, the grooves 41 assure smooth guidance of a target solution to be measured 9 to the opening 4.

Figure 8:
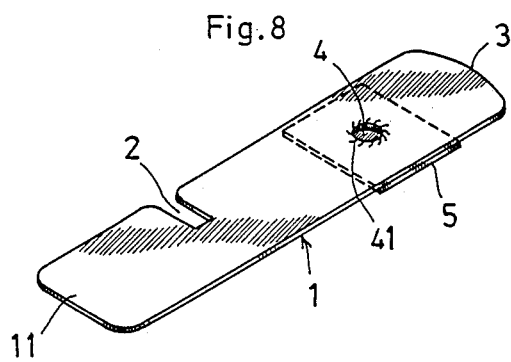

Each of the grooves 41 is not required to be linear as shown in FIG. 7, but may be spiral as shown in FIG. 8 showing a fourth embodiment of the present invention.

Figure 9:
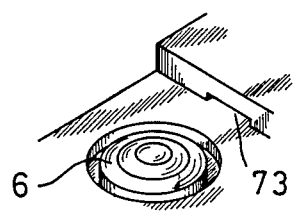
FIG. 9 is a schematic perspective view of main portion of another example of a sensor.

In the sensor, the shorter-side engagement portion is not limited to the arrangement having the engagement concave 71 and the projection 72 shown in FIGS. 3 and 4. Such shorter-side engagement portion may be formed by a slit 73 only as shown in FIG. 9. With the use of the slit 73, the thin resilient plate 1 may be easily mounted and removed as done with the arrangement shown in FIGS. 3 and 4.

In the diffusion-limiting membrane holding means for the sensor shown in FIG. 1 to FIG. 8, it is preferable to turn the holding-portion side of the thin resilient plate 1 in the form of a mountain to enhance the strength thereof.

In accordance with a fifth embodiment of the present invention in FIG. 10 (A), (B) and (C), a thin resilient plate 1 has a narrower holding-portion side and a wider end side 3 which is provided with a positioning notched concave 31 (See FIG. 10 (A)) or which is provided with a positioning projection 32 (See FIG. 10 (C)).

Further, the thin resilient plate 1 may have, as a wider side, a circular portion which is provided at a predetermined position of the periphery thereof with at least one positioning notched concave 31, as shown in FIG. 11 (A). As shown in FIG. 11 (B), the thin resilient plate 1 may have a positioning hole 33 formed at a predetermined position in the vicinity of one end side thereof.

Further, one shorter side and a predetermined portion of one longer side of the thin resilient plate of which the ratio of the longer side to the shorter side is considerable or not so considerable, may be used, as they are, as positioning engagement portions. It is noted that such arrangement is not shown in the attached drawings.

When the diffusion-limiting membrane holding means having the arrangement shown in FIGS. 10 or 11, is used, the engagement portion 7 of the sensor may have a projection which is adapted to be engaged with the notched concave or hole, or the engagement portion 7 of the sensor may have a cutaway portion which is adapted to be engaged with the projection, whereby accurate positioning is assured.

Figure 12:
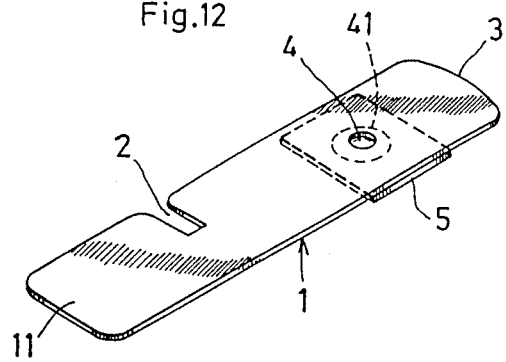
FIG. 12 is a perspective view of a diffusion-limiting membrane holding means for a sensor in accordance with a seventh embodiment of the present invention.
Figure 13:
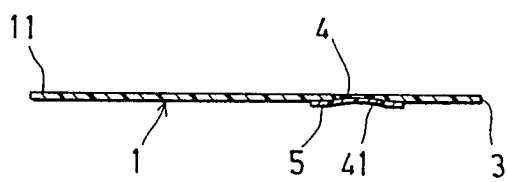
FIG. 13 is a vertical section view of the center portion of the means in FIG. 12.

FIG. 12 is a perspective view of a seventh embodiment of the present invention, while FIG. 13 is a vertical section view thereof.

The seventh embodiment is the same as the first embodiment in FIG. 1, except that a thin resilient plate 1 in FIG. 12 is provided at a predetermined area thereof including an opening 4 with a concave 41 having a radius of curvature substantially equal to that of the surface of the enzyme electrode unit 6, a diffusion-limiting membrane 5 being attached as covering this concave 41.

When the diffusion-limiting membrane 5 attached to diffusion-limiting membrane holding means for a sensor having the arrangement in FIG. 12 is pressed to the enzyme electrode unit 6, the diffusion-limiting membrane 5 may be stuck to the enzyme electrode unit 6 in a wide range and the pressing force exerted to the stuck portion may be substantially uniform. Accordingly, when the diffusion-limiting membrane 5 is replaced, the reproducibility of the adhesion of the diffusion-limiting membrane 5 and the enzyme electrode unit 6 may be considerably enhanced, assuring stable measurement with high precision. Further, the arrangement in FIG. 12 prevents a great pressing force from being only locally applied to the diffusion-limiting membrane 5 and an enzyme-immobilized membrane attached to the enzyme electrode unit 6. This considerably restrains the deterioration of the characteristics of both membranes, in particular the enzyme-immobilized membrane.

Although not shown, the same concave as the concave 41 in FIGS. 12 and 13 may be formed in the diffusion-limiting membrane holding means for a sensor shown in FIG. 6 to FIG. 8, FIG. 10 and FIG. 11. In such case, the same effects as above-mentioned may be achieved.

Figure 14:
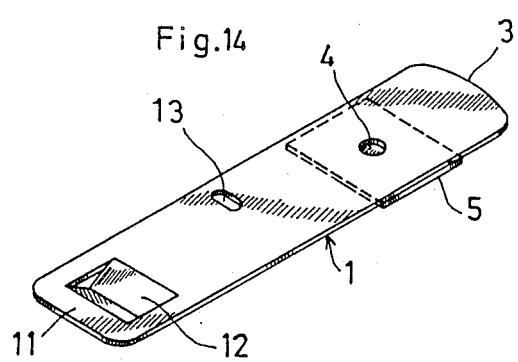
FIG. 14 is a perspective view of a diffusion-limiting membrane holding means for a sensor in accordance with an eighth embodiment of the present invention.
Figure 15:
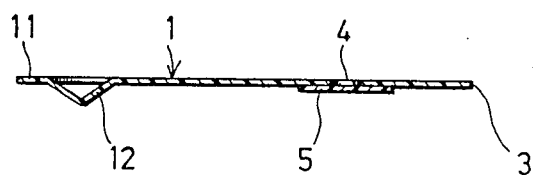
FIG. 15 is a vertical section view of the center portion of the means in FIG. 14.

FIG. 14 is a perspective view of an eighth embodiment of the present invention, while FIG. 15 is a vertical section view thereof. The eighth embodiment is the same as the first embodiment in FIG. 1, except in the following three points.

In the eighth embodiment, one longer side of a thin resilient plate 1 is used, as it is, as an engagement portion, and the thin resilient plate 1 has a holding portion 11 provided at a predetermined position thereof with a projecting portion 12 which projects to the diffusion-limiting membrane mounting side. Further, the thin resilient plate 1 has a positioning hole 13 at a predetermined position of the center thereof.

When mounting the diffusion-limiting membrane holding means in FIG. 14 on the sensor having the arrangement in FIG. 9, the sensor may have, at a position opposite to the slit 73, a thin resilient plate regulating member (not shown) which is vertically movable, and a positioning shaft (not shown) in the vicinity of the enzyme electrode unit. With one shorter side 3 engaged with the slit 73 and the positioning hole 13 faced to the positioning shaft, the thin resilient plate regulating member may be vertically moved. Thus, there may be easily selected a state where a diffusion-limiting membrane 5 is pressed to the enzyme electrode unit 6, or a state where the the diffusion-limiting membrane 5 is separated from the enzyme electrode unit 6.

When the the diffusion-limiting membrane holding means for a sensor having the arrangement in FIG. 14 is put on an arbitrary place, the holding portion 11 is kept as raised, facilitating to hold the diffusion-limiting membrane holding means for a sensor with the hand. Further, when a target solution to be measured is dropped on an opening 4 with the diffusion-limiting membrane holding means put on an arbitrary place, it takes a certain measure of time before the dropped target solution penetrates through the diffusion-limiting membrane 5. This considerably decreases the possibility that the arbitrary place above-mentioned is wetted by the target solution to be measured.

When the same projecting portion as the projecting portion 12 in FIGS. 14 and 15 is formed in the diffusion-limiting membrane holding means for the sensor in FIG. 6 to FIG. 8, FIG. 10 and FIG. 11, the same effect as that above-mentioned can be achieved.

Figure 16A:
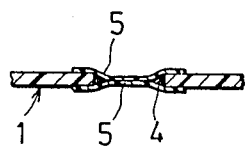
FIGS. 16a and b are vertical section views of the center portion of the diffusion-limiting membrane holding means for a sensor in accordance with a still another embodiment of the present invention.
Figure 16B:
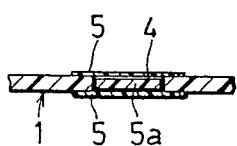

The projecting portion 12 may have a circular section or may be formed by turning an end of the thin plate 1. Further, the projecting portion 12 may project on that surface of the thin resilient plate 1 on which the diffusion-limiting membrane 5 is mounted or not mounted, or may project on both surfaces of the thin plate 1. In the embodiments above-mentioned, the diffusion-limiting membrane 5 may be attached to both sides of the thin plate 1 (See FIG. 16 (A)). Further in the embodiments above-mentioned, the diffusion-limiting membrane 5 may be attached to both sides of the thin plate 1 so as to maintain a membrane 5a positioned in the opening 4 having a high penetration ratio of the target solution (See FIG. 16 (B)).

When the target solution to be measured 9 is to be dropped to the diffusion-limiting membrane holding means for a sensor having the arrangement in FIG. 14, the target solution may be dropped on the thin resilient plate 1 in the vicinity of the opening with the diffusion-limiting membrane holding means for a sensor put on a flat place. This assures a more reliable and simplified dropping operation as compared with the case where a target solution is dropped with the the diffusion-limiting membrane holding means for the sensor mounted on the sensor. Further, the thin resilient plate 1 is slightly raised by the projecting portin 12. This not only prevents the target solution from being moved to the flat place, but also facilitates to lift up the diffusion-limiting membrane holding means for a sensor upon completion of dropping the target solution to be measured.

Figure 17:
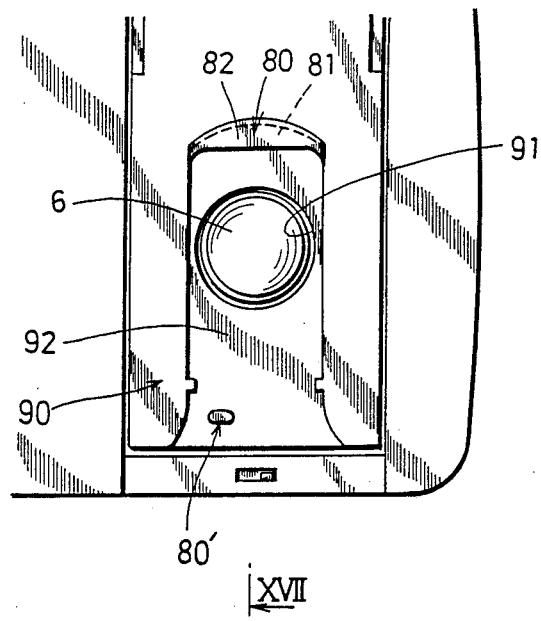
FIG. 17 is a plan view of main portions of a sensor on which the diffusion-limiting membrane holding means for a sensor in FIG. 14 is suitably mounted.
Figure 18:
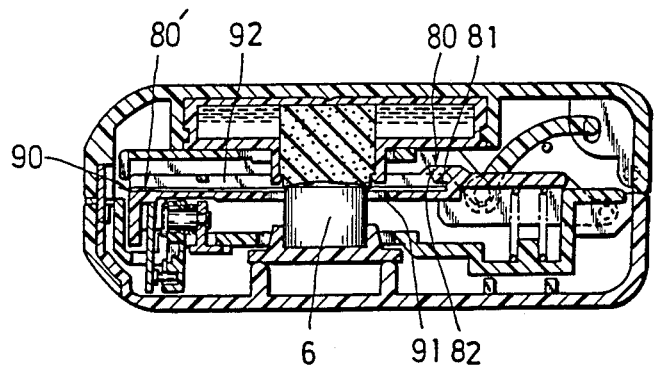
FIG. 18 is a longitudinal section view taken along the line XVIII—XVIII in FIG. 17.

FIG. 17 is a plan view of a sensor on which the diffusion-limiting membrane 5 is suitably mounted with the use of the diffusion-limiting membrane holding means for the sensor in FIGS. 14 and 15, while FIG. 18 is a vertical section view thereof.

The sensor has a base stand, an enzyme electrode unit 6 mounted at a predetermined position of the base stand such that the electrode unit surface projecting upward, and a mounting member 90 for mounting the diffusion-limiting membrane holding means for the sensor. This mounting member 90 includes: a through-hole 91 into which the enzyme electrode unit 6 is inserted; a housing groove 92 for housing the diffusion-limiting membrane holding means for a sensor; and engagement portions 80 and 80' at predetermined positions thereof, i.e., at the innermost position and a predetermined position of the side at which the diffusion-limiting membrane holding means for a sensor is mounted or removed.

More specifically, the engagement portion 80 has, at the inner part thereof, an arcuate engagement concave 81 having the same radius of curvature as that of the shorter side 3, and a projection 82 which constitutes an upper regulating projection of the engagement concave 81.

The projection 82 may have a wide width covering the entire width of the engagement concave 81, or may have a width narrower than the entire width of the engagement concave 81. The engagement portion 80' is a standing portion having the substantially same plane shape as that of the positioning hole 13. The enzyme electrode unit 6 has a substantially arcuate surface.

A diffusion-limiting membrane attached to the diffusion-limiting membrane holding means for a sensor in accordance with the present invention may be mounted on the sensor having the arrangement in FIG. 17 in the following manner.

Figure 19:
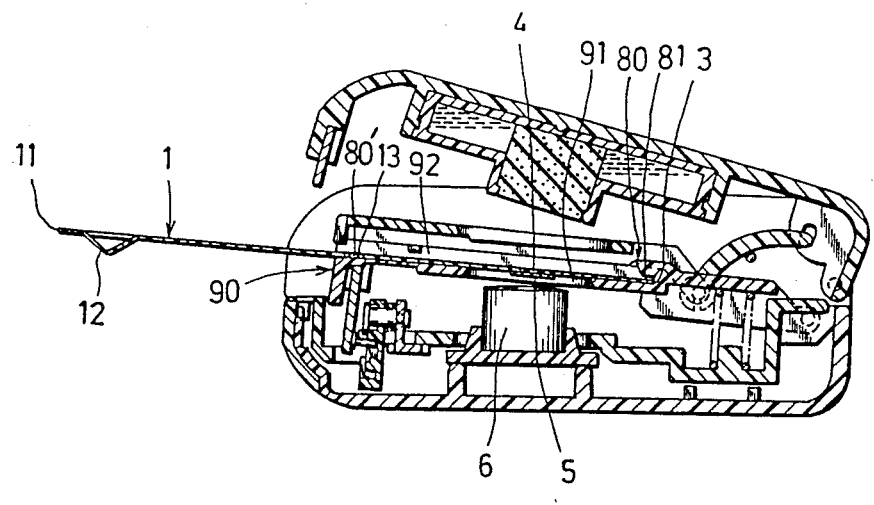
FIGS. 19a and b are views illustrating how to mount the diffusion-limiting membrane holding means for a sensor in accordance with the present invention.
Figure 19:
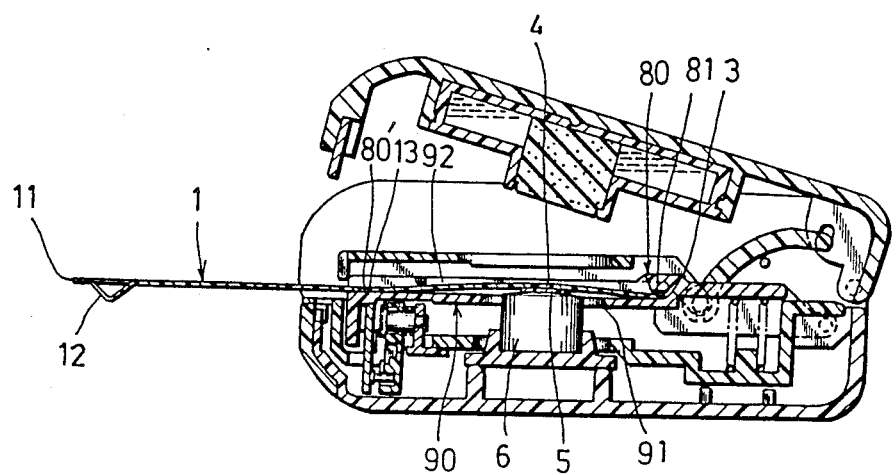

With the diffusion-limiting membrane 5 positioned at the underside of the thin resilient plate 1, the shorter side 3 of the thin resilient plate 1 is inserted into the engagement concave 81. The mounting member 90 for mounting the diffusion-limiting membrane holding means is then moved downward with the thin resilient plate 1 housed in the housing groove 92 such that the diffusion-limiting membrane 5 is opposite to the through-hole 91 (See FIG. 19 (A)). This causes the surface of the enzyme electrode unit 6 to project from the through-hole 91 such that this surface is stuck to the diffusion-limiting membrane 5 mounted on the diffusion-limiting membrane holding means for a sensor (See FIG. 19 (B)).

In such state, the target solution to be measured 9 reaches to the diffusion-limiting membrane 5 through the opening 4. The solution is guided to the enzyme electrode unit 6 with a target substance to be measured in the solution limited in diffusion by the diffusion-limiting membrane 5 to lower the concentration of the target substance to some extent. Accordingly, even though the concentration of a target substance in a target solution is originally high, measurement can be made with the concentration of the target substance considerably lowered.

Upon completion of the measurement, the diffusion-limiting membrane holding means for a sensor may be easily removed by reversing the mounting operations above-mentioned.

Figure 20A:
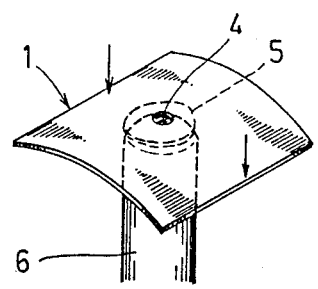
FIGS. 20a and b are is a perspective views of a diffusion-limiting membrane holding means for a sensor in accordance with a still further embodiment of the present invention together with an enzyme electrode unit.
Figure 20B:
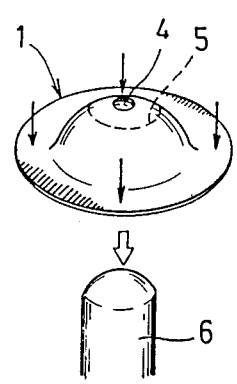

FIG. 20 shows a still further embodiment of the diffusion-limiting membrane holding means for a sensor in accordance with the present inventions respectively.

This embodiment is considerably different from the foregoing embodiments in that a thin resilient plate 1 is square plate (See FIG. 20 (A)) or dishlike plate (See FIG. 20 (B)).

More specifically, the thin resilient plate 1 has an opening 4 in the center portion thereof and a diffusion-limiting membrane 5 is attached to the thin resilient plate 1 to cover the opening 4.

When the diffusion-limiting membrane 5 is to be stuck to the enzyme electrode unit 6, downward force may be applied to the outward portion of the thin resilient plate 1. Then, the thin resilient plate 1 is resiliently bent to enable the diffusion-limiting membrane 5 to be securely stuck to the surface of the enzyme electrode unit 6.

Figure 21:
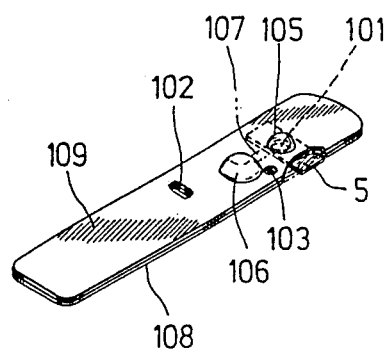
FIG. 21 is a perspective view of a diffusion-limiting membrane holding means for a sensor in accordance with a ninth embodiment of the present invention, the means having a housing portion for housing a standard solution for calibration.
Figure 22:
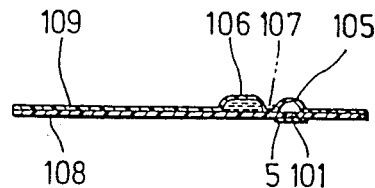
FIG. 22 is a vertical section view of the center portion of the means in FIG. 20.

FIG. 21 is a perspective view of a ninth embodiment of the diffusion-limiting membrane holding means for a sensor in accordance with the present invention, while FIG. 22 is a vertical section view of the center portion thereof.

The ninth embodiment is considerably different from the eighth embodiment in FIGS. 14 and 15 in that a housing portion for housing a standard solution for calibration 106 is disposed.

More specifically, the diffusion-limiting membrane holding means for a sensor in FIG. 21 has a long-size plate 108 and a sheet 109 integrally stuck to the plate 108, both plate 108 and sheet 109 having the same plane shape as that of the holding means of the eighth embodiment in FIG. 14. The plate 108 has in its predetermined position, an opening 101 which is adapted to become opposite to the enzyme electrode unit 6 when the diffusion-limiting membrane holding means for a sensor in FIG. 21 is mounted on a sensor. The plate 108 and the sheet 109 have openings 102 and 103 which are adapted to be opposite to positioning portions(not shown) of the sensor. A diffusion-limiting membrane 5 is attached to the underside of the plate 108 as covering the opening 101. To cover the top side of the opening 101, the sheet 109 is curved to form a surrounding portion 105. The sheet 109 is also curved to form a housing portion 106 for housing a standard solution for calibration at a position in the vicinity of the surrounding portion 105. There is formed a guide portion 107 through which the surrounding portion 105 and the housing portion 106 communicate with each other.

Figure 23:
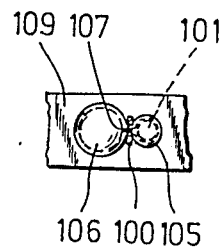
FIG. 23 is a plan view of main portions of a method of making the diffusion-limiting membrane holding means for a sensor in FIGS. 19 and 20.

More specifically, the surrounding portion 105, the housing portion 106 and the guide portion 107 are simultaneously formed by meltingly bonding the sheet 109 to the long-size plate 108 by a heat sealing method. As shown in FIG. 23, heat sealing may be carried out with different adhesives locally disposed between the plate 108 and the sheet 109, thereby to form a weakly bonded portion 100 having a weak adhesion force. This weakly bonded portion 100 may be used as the guide portion 107. Alternatively, the heat sealing temperature may be locally lowered to thin the thickness of the melting bonded portion. Such portion having a thinner thickness may be used as the guide portion 107.

Prior to measurement of the concentration of a target substance, the diffusion-limiting membrane holding means for a sensor having the housing portion 106 for housing a standard solution for calibration may be mounted on the sensor having the arrangement in FIGS. 17 and 18. Then, the mounting member 90 for mounting the diffusion-limiting membrane holding means may be rotated downward, such that the diffusion-limiting membrane 5 and the enzyme electrode unit 6 are pressed to each other. Then, the housing portion 106 may be crushed to guide the standard solution for calibration to the surrounding portion 105 through the guide portion 107. Accordingly, the standard solution may be guided to the surface of the enzyme electrode unit 6 through the diffusion-limiting membrane 5. The enzyme electrode unit 6 may generate a detection signal corresponding to the standard solution for calibration having a known concentration of a target substance. Based on the detection signal thus generated, an initial calibration operation may be carried out.

After such initial calibration operation has been finished, the diffusion-limiting membrane holding means having the housing portion 106 may be removed, and the diffusion-limiting membrane holding means for a sensor (See FIGS. 14 and 15) to the opening 4 of which a target solution to be measured having unknown concentration has been dropped, on the mounting member 90. With the surface of the electrode unit 6 stuck to the diffusion-limiting membrane 5, an electric signal may be taken out the enzyme electrode unit 6. Based on the electric thus taken out, the concentration of the target su to be measured may be calculated.

Figure 24:
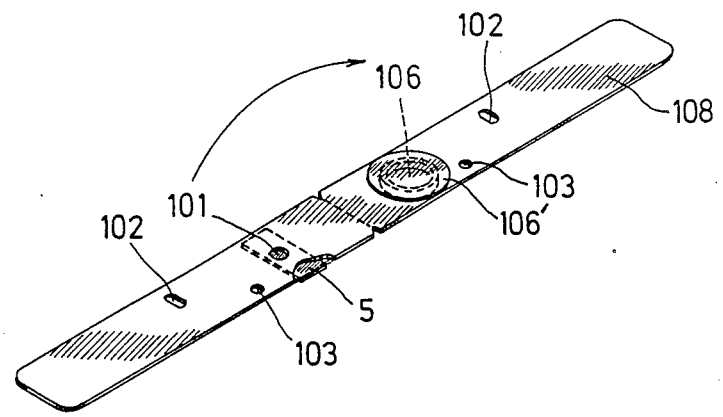
FIG. 24 is a perspective view of a diffusion-limiting membrane hOlding means for a sensor in accordance with a tenth embodiment of the present invention, the means having a housing portion for housing a standard solution for calibration.

FIG. 24 is a perspective v of a tenth embodiment of the diffusion-limiting holding means for a sensor in accordance with the invention.

The tenth embodiment is same as the ninth embodiment in FIGS. 21 and in the following two points only.

In FIG. 24, a long-size 108 has a length twice that of the long-size plate 108 in FIGS. 14 and 15, and may be piled up as folded at the center thereof. One half-portion of the plate has an opening 101 and a diffusion-limiting membrane and the other halfportion thereof has a housing 106 for housing a standard solution for calibration and a removable seal 106'.

With such arrangement, the 108 may be folded with the seal 106' removed. An calibration operation may be carried out with the folded plate 108 mounted on the mounting member 90 of the sensor.

Figure 25:
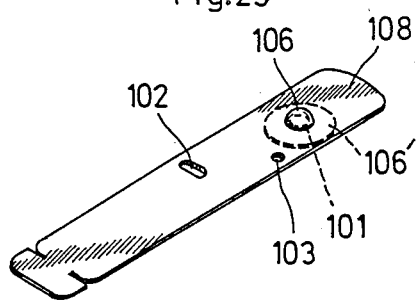
FIG. 25 is a perspective view of a diffusion-limiting membrane holding means for a sensor in accordance with an eleventh embodiment of the present invention, the means having a housing portion for housing a standard solution for calibration.

FIG. 25 is a perspective view of an eleventh embodiment of the diffusion-limiting membrane holding means for a sensor in accordance with the present invention.

The means in FIG. 25 is different from the ninth embodiment in FIGS. 21 and 22 in the following points.

In the means in FIG. 25, instead of forming an opening passing through a long-size plate 108, the long-size plate 108 is locally curved to form an opening 101 and a housing portion 106 for housing a standard solution for calibration at the same time, and a removable seal 106' is disposed on the opening 101.

In the means in FIG. 25, since a diffusion-limiting membrane is omitted, it is required to use care on liquid leakage after the seal 106' has been removed. However, the entire structure can be considerably simplified.

In the embodiment in FIGS. 21 and 22, a guide portion having a small section area may be disposed, instead of the guide portion 107 which is weakly bonded to the long-size plate 108. Further, the long-size plate 108 in FIGS. 21 and 22 may have a plane shape different from that of the diffusion-limiting membrane holding means for the sensor in FIGS. 14 and 15, or may have the same plane shape as that of the diffusion-limiting membrane holding means for the sensor shown in FIG. 1, FIGS. 6 to 8, FIGS. 10 to 12 or FIG. 14. The sheet 109 may be molten at necessary portions only.

What is claimed is:

1. A diffusion-limiting membrane holding means for a sensor, comprising:
   a thin resilient plate provided in a predetermined position with an opening through which a target solution to be measured is adapted to penetrate, said thin resilient plate adapted to be bent into operative position; and
   a diffusion-limiting membrane for limiting diffusion of the target solution attached to said thin resilient plate so as to cover said opening, and said diffusion-limiting membrane being dimensioned and attached to said resilient plate such that, upon a bending of said resilient plate into operative position, said plate causes a similar bending in said attached membrane.

2. A diffusion-limiting membrane holding means for a sensor as set forth in claim 1, wherein said surface of the thin resilient plate is hydrophobic and a wall defining said opening is hydrophilic.

3. A diffusion-limiting membrane holding means for a sensor as set forth in claim 1, wherein said thin resilient plate is provided at its predetermined area including the opening with an arcuate concaved portion.

4. A diffusion-limiting membrane holding means for a sensor as set forth in claim 1, wherein the opening is provided at the periphery thereof with a plurality of acute convexo-concave portions.

5. A diffusion-limiting membrane holding means for a sensor as set forth in claim 1, wherein said thin resilient plate is provided with a plurality of grooves at the periphery of the opening, said grooves extending outward around said opening.

6. A diffusion-limiting membrane holding means for a sensor as set forth in claim 5, wherein each of the grooves is spiral.

7. A diffusion-limiting membrane holding means for a sensor as set forth in claim 1, wherein said thin resilient plate is provided at a predetermined position thereof with a projection for holding said thin resilient plate in a raised portion.

8. A diffusion-limiting membrane holding means for a sensor as set forth in claim 7, wherein said thin resilient plate is provided with the projection at only a position thereof remote from the opening.

9. A diffusion-limiting membrane holding means for a sensor as set forth in claim 7, wherein the surface of said thin resilient plate is hydrophobic and the wall of the opening is hydrophilic.

10. A diffusion-limiting membrane holding means for a sensor as set forth in claim 1, wherein said thin resilient plate is provided at a predetermined position thereof with a housing portion for housing a standard solution for calibration, said housing portion being adapted to supply the standard solution for calibration to the opening.

11. A diffusion-limiting membrane holding means for a sensor as set forth in claim 10, wherein said thin resilient plate has a guide portion adapted to guide the standard solution for calibration to the opening only when the housing portion is crushed.

12. A diffusion-limiting membrane holding means for a sensor as set forth in claim 11, wherein a long-size plate and a sheet are laminated to each other, and a housing portion for housing standard solution for calibration and a guide portion are formed between said long-size plate and said sheet.

13. A diffusion-limiting membrane holding means for a sensor as set forth in claim 10, wherein said thin resilient plate has a surrounding portion which covers the top side of said opening and which connects with the guide portion.

14. A diffusion-limiting membrane holding means for a sensor comprising:
   a thin resilient plate lengthened in one direction and provided in a predetermined position with an opening through which a target solution to be measured is adapted to penetrate; and
   a diffusion-limiting membrane for limiting diffusion of the target solution attached to said thin resilient plate so as to cover said opening;
   one longitudinal end side of said thin resilient plate serving as an engagement side adapted to be engaged with one of a pair of positioning portions disposed on a sensor, the positioning portions being opposite to each other with respect to an enzyme electrode unit of the sensor;
   the other longitudinal end side of said thin resilient plate serving as a holding portion;
   one longer side of said thin resilient plate having engagement means for engagement with the other of the positioning portions and the distance between said engagement side and engagement means being greater than the distance between the pair of positioning portions so as to cause said thin resilient plate to bow outwardly so as to essentially conform to a curved surface of the electrode.

15. A diffusion-limiting membrane holding means for a sensor as set forth in claim 14, wherein said one longitudinal end side of the thin resilient plate is arcuate around the center of the opening.

16. A diffusion-limiting membrane holding means for a sensor as set forth in claim 14, wherein said one longitudinal end side of the thin resilient plate is provided at a predetermined position thereof with a positioning notched concave.

17. A diffusion-limiting membrane holding means for a sensor as set forth in claim 14, wherein said one longitudinal end side of the thin resilient plate is provided at a predetermined position thereof with a positioning projection.

18. A diffusion-limiting membrane holding means for a sensor as set forth in claim 14, wherein the thin resilient plate is provided with a positioning hole at a predetermined position thereof in the vicinity of said one longitudinal end side.

19. A diffusion-limiting membrane holding means for a sensor as set forth in claim 14, wherein said engagement means is a notched groove.

20. A diffusion-limiting membrane holding means for a sensor as set forth in claim 14, wherein said engagement means is a stepped portion.

21. A diffusion-limiting membrane holding means for a sensor comprising:
a thin resilient plate lengthened in one direction provided in a predetermined position thereof with an opening through which a target solution to be measured is adapted to penetrate; and
a diffusion-limiting membrane for limiting diffusion of said target solution attached to said thin resilient plate as covering said opening;
one longitudinal end side of said thin resilient plate serving as an engagement side adapted to be engaged with one of a pair of positioning portions disposed on a sensor, said positioning portions being opposite to each other with respect to an enzyme electrode unit of said sensor;
the other longitudinal end side of said thin resilient plate serving as a holding portion;
one longer side of said thin resilient plate serving as an engagement portion adapted to be engaged with the other of said positioning portions, wherein said one longitudinal end side of the thin resilient plate is arcuate around the center of the opening.

22. A diffusion-limiting membrane holding means for a sensor, comprising:
a thin resilient plate having formed therein an opening through which a target solution to be measured is adapted to penetrate, said thin resilient plate having an elongated length and said thin resilient plate having a cross-sectional thickness which is essentially equal over the entire elongated length of said thin resilient plate; and
a diffusion-limiting membrane for limiting diffusion of the target solution attached to said thin resilient plate so as to cover said opening.

* * * * *